(12) United States Patent
Daniels (10) Patent No.: US 12,004,585 B2
(45) Date of Patent: Jun. 11, 2024

(54) WELDING HELMET

(71) Applicant: 3M INNOVATIVE PROPERTIES COMPANY, St. Paul, MN (US)

(72) Inventor: Björn Daniels, Vikarbyn (SE)

(73) Assignee: 3M Innovative Properties Company, St. Paul, MN (US)

(*) Notice: Subject to any disclaimer, the term of this patent is extended or adjusted under 35 U.S.C. 154(b) by 186 days.

(21) Appl. No.: 17/596,510

(22) PCT Filed: Jul. 1, 2020

(86) PCT No.: PCT/IB2020/056224
§ 371 (c)(1),
(2) Date: Dec. 13, 2021

(87) PCT Pub. No.: WO2021/005461
PCT Pub. Date: Jan. 14, 2021

(65) Prior Publication Data
US 2022/0312881 A1   Oct. 6, 2022

(30) Foreign Application Priority Data
Jul. 5, 2019   (EP) ..................................... 19184715

(51) Int. Cl.
*A42B 3/10*   (2006.01)
*A42B 3/22*   (2006.01)
*A61F 9/06*   (2006.01)
(52) U.S. Cl.
CPC ................ *A42B 3/10* (2013.01); *A42B 3/225* (2013.01); *A61F 9/067* (2013.01)

(58) Field of Classification Search
CPC ................................ A42B 3/225; A61F 9/067
See application file for complete search history.

(56) References Cited

U.S. PATENT DOCUMENTS

| | | | | |
|---|---|---|---|---|
| 4,051,555 A * | 10/1977 | Daly | ........................ | A42B 3/14 2/6.6 |
| 4,675,919 A * | 6/1987 | Heine | ..................... | A61B 90/50 2/181 |
| 5,025,504 A * | 6/1991 | Benston | ................... | A42C 5/02 2/181.8 |
| 5,673,431 A | 10/1997 | Batty | | |
| 6,966,074 B2 * | 11/2005 | Huh | ......................... | A42B 3/14 2/416 |
| 9,814,622 B2 | 11/2017 | Sommers | | |

(Continued)

FOREIGN PATENT DOCUMENTS

| | | |
|---|---|---|
| KR | 1020130025534 | 3/2013 |
| WO | WO 2019-058282 | 3/2019 |

OTHER PUBLICATIONS

International Search Report for PCT International Application No. PCT/IB2020/056224, dated Sep. 15, 2020, 5 pages.

*Primary Examiner* — Khaled Annis (57) ABSTRACT

There is provided a welding helmet (1) comprising a face protection member (3) moveable between a lowered position in which the face protection member (3) covers a wearer's face, and an upraised position, in which the face protection member (3) uncovers the wearer's face, a headband suspension system (9) for fixing the face protection member (3) to a wearer's head, a protective cap (17) comprising a flexible outer layer (19) and at least one compressible inner liner (21).

20 Claims, 5 Drawing Sheets

(56) References Cited

U.S. PATENT DOCUMENTS

| | | | |
|---|---|---|---|
| 2007/0245466 A1* | 10/2007 | Lilenthal | A42B 3/14 2/416 |
| 2007/0245467 A1* | 10/2007 | Lilenthal | A42B 3/225 2/416 |
| 2008/0060102 A1* | 3/2008 | Matthews | F16P 1/06 2/8.2 |
| 2010/0223707 A1* | 9/2010 | Moyses | A42B 3/225 2/8.2 |
| 2014/0237706 A1 | 8/2014 | O'Conner | |
| 2014/0259318 A1* | 9/2014 | Daniels | A42B 3/225 2/424 |
| 2015/0113712 A1* | 4/2015 | Hirschmann, Jr. | A61F 9/065 2/424 |
| 2015/0201696 A1* | 7/2015 | Pfanner | A42B 3/225 2/424 |
| 2015/0359677 A1* | 12/2015 | Sommers | A42B 3/225 2/8.2 |
| 2016/0074230 A1 | 3/2016 | Sernfält | |
| 2016/0361201 A1 | 12/2016 | Sommers | |
| 2017/0027269 A1* | 2/2017 | Wilson | A42C 5/02 |
| 2017/0164677 A1 | 6/2017 | Olivares Velasco | |
| 2017/0255027 A1* | 9/2017 | Hofer-Kraner | A61F 9/067 |
| 2019/0029355 A1* | 1/2019 | Seo | A61F 9/06 |
| 2020/0205507 A1* | 7/2020 | Sernfält | A61F 9/06 |
| 2020/0289323 A1* | 9/2020 | Daniels | A61F 9/064 |
| 2020/0297060 A1* | 9/2020 | Berggren | A42B 3/225 |
| 2020/0405000 A1* | 12/2020 | Nilsson | A42B 3/127 |
| 2022/0000667 A1* | 1/2022 | Frejd | A42B 3/225 |
| 2022/0071334 A1* | 3/2022 | Huang | A42B 3/222 |
| 2022/0312881 A1* | 10/2022 | Daniels | A42B 3/225 |

* cited by examiner

WELDING HELMET

TECHNICAL FIELD

The present disclosure relates to a welding helmet comprising a face protection member moveable between a lowered position in which the face protection member covers a wearer's face, and an upraised position, in which the face protection member uncovers the wearer's face, a headband suspension system for fixing the face protection member to a wearer's head.

BACKGROUND OF THE DISCLOSURE

Welding Helmets are typically used in the mechanical and industrial art to protect wearers from harmful irradiation emitted from the welding arc and from splashes, sparks and particles that may be ejected from a welding area. Welding helmets typically can be suspended on the head of a wearer, so that the wearer has both hands available for welding and handling of workpieces.

Some welding helmets are furnished with an automatic darkening filter. An automatic darkening filter commonly has a switchable filter that automatically changes from a light-state to a dark-state in response to incident light generated by the welding arc. Thus, upon ignition of the welding arc the switchable filter automatically changes to the dark-state and protects the wearer's eyes and face from the irradiation emitted from welding arc. Once the welding is interrupted or ended the switchable filter automatically changes to the light-state so that the wearer can see through the filter at normal light conditions.

Often the wearer is working in close proximity to the workpiece or even inside the workpiece in the case of pipe welding for example. As a result, the wearer's head may be inside workpieces or in close proximity to the workpiece. Therefore, it is not uncommon for the wearer's head to be covered in dirt and other fragments from the workpiece. It is also not uncommon for the wearer to bump or scrape their head on hard or sharp objects from the workpiece.

It is not possible to wear separate head protection in conjunction with such welding helmets as described above, therefore it is known to provide the wearer with a bump cap to offer a degree of protection against injury. These bump caps have a rigid or semi-rigid shell.

For example, US2016/0361201 A1 discloses a system for attaching a bump cap to welding headgear.

These known bump caps are often heavy, large and inflexible and therefore cause discomfort to the wearer.

There remains a need for a protective cap for a welding helmet, which provides improved comfort to the wearer while also being able to protect the wearer's head from welding safety risks.

SUMMARY

According to a first aspect of the invention there is provided a welding helmet comprising:
 a face protection member moveable between a lowered position in which the face protection member cover's a wearer's face, and an upraised position, in which the face protection member uncovers the wearer's face,
 a headband suspension system for fixing the face protection member to a wearer's head and,
 a protective cap comprising a flexible outer layer and at least one compressible inner liner.

According to a second aspect of the invention there is provided a use of a protective cap for a welding helmet comprising a face protection member as well as a headband suspension system for fixing the face protection member to a wearer's head, wherein the protective cap comprises a flexible outer layer and at least one compressible inner liner.

The face protection member moveable between a lowered position in which the face protection member cover's a wearer's face, and an upraised position, in which the face protection member uncovers the wearer's face provides the advantage that allows for swivelling of the face protection member out of a wearer's field of vision relatively quickly without having to take the entire helmet of the head and put it back afterwards. It also allows the face protection member to be held in the upraised position, which is useful when then wearer is not welding and wishing to communicate or handling workpieces or welding equipment.

The headband suspension system for fixing the face protection member to a wearer's head is advantageous because it ensures the welding helmet and face protection member are securely fixed on a wearer's head. There may be situations where the wearer is working in narrow spaces and must look up to weld. The welding helmet must have a secure fit to the wearer's head to ensure there is the appropriate protection at all times.

The flexible outer layer and at least one compressible inner liner of the protective cap provide an advantageous combination to the wearer. The flexible outer layer of the protective cap provides a close fit to the wearer's head therefore improving and maximising the comfort to the wearer. The flexibility of the outer layer provides improved conformability to the wearer's head and again improves comfort compared to known bump caps which are often rigid or semi-rigid and therefore are not conformable. The flexible outer layer also prevents the protective cap from slipping from the wearer's head, further increasing comfort to the wearer. It also provides protection to dirt and other fragments falling from the workpiece. The compressible inner liner of the protective cap provides protection to the wearer from small bumps and scrapes. The compressible feature of the inner liner can absorb the minor bumps or scrapes the wearer may encounter. The at least one compressible inner liner can change in volume when a pressure is applied to it, for example if the wearer hit their head it would decrease in volume to absorb the force, reducing risk of injury. The flexible outer layer and the compressible inner liner provide increased comfort to the wearer, whilst also providing an appropriate level of protection for the environment the wearer is working in.

The face protection member may comprise a moveable visor and/or the moveable visor may comprise an automatic darkening filter. There may be also systems available without a moveable visor but that do comprise an automatic darkening filter.

The moveable visor allows the wearer to see when they are welding and when they are not welding. This provides a welding helmet which is easier to use, as the whole helmet does not have to be removed from the head each time the wearer stops welding. The automatic darkening filter allows a wearer to safely observe the welding arc during welding.

According to another embodiment, the protective cap comprises a first attachment means for attaching the protective cap to the headband suspension system.

This feature allows the welding helmet to be worn with and without the protective cap. This allows flexibility to the wearer depending on the environment they are working in. This feature also allows the protective cap to be cleaned separately to the welding helmet. Furthermore, when the protective cap is attached the welding helmet, it is more secure on the wearer's head and provides better fit and improved comfort to the wearer.

According to another embodiment, the first attachment means comprises a hook and loop attachment means, sewing means, clip means or adhesive means. All these means are well known in the art and are easy to integrate into a welding helmet as well as easy to use for a wearer.

According to another embodiment, the protective cap is attached under the headband suspension system.

In the context of this disclosure, "under" means the protective cap is situated below the headband suspension system, between the wearer's head and the headband suspension system.

This feature ensures there is a close fit of the protective cap to the wearers head. Consequently, comfort to the wearer is maximised. Furthermore, the headband suspension system can be adjusted without the wearer's having to remove the protective cap as it is still accessible.

According to another embodiment, the compressible inner liner of the protective cap is permanently or removably attached to an inside surface of the flexible outer layer of the protective cap.

In the context of this disclosure, "inside surface" means a surface that faces the wearer's head.

When the inner liner of the protective cap is permanently attached to the inside surface of the flexible outer layer of the protective cap the inner liner is more secure and will not move around inside the protective cap. This provides improved comfort to the wearer.

When the inner liner of the protective cap is removably attached to the inside surface of the flexible outer layer of the protective cap, the inner liner can be removed, cleaned and replaced or it can be removed and replaced to the inside surface of the flexible outer layer. This ensures the inner liner is in the proper condition for the wearer. Furthermore, the whole protective cap does not need to be replaced when the condition of the inner liner deteriorates only the inner liner needs to be replaced.

The inner surface of the flexible outer layer may also comprise a non-slip material to prevent the protective cap from moving around on the wearer's head. The non-slip material may be in areas where the inner liner is not located, for example on the sides of the protective cap facing the wearer's head.

According to another embodiment, the compressible inner liner of the protective cap is attached to the inside surface of the flexible outer layer of the protective cap using a second attachment means.

When the inner liner of the protective cap is removably attached to the inside surface of the flexible outer layer of the protective cap using a second attachment means, the inner liner can be removed, cleaned and replaced or it can be removed and replaced to the inside surface of the flexible outer layer. This ensures the inner liner is in the proper condition for the wearer. Furthermore, the whole protective cap does not need to be replaced when the condition of the inner liner deteriorates as only the inner liner needs to be replaced.

According to another embodiment, the second attachment means is any one of a hook and loop attachment means, sewing means, clip means, adhesive means. All these means are well known in the art and are easy to integrate into a welding helmet.

The at least one compressible inner liner of the protective cap may be of a uniform thickness.

This feature makes it simple to manufacture the compressible inner liner. Also, the cost of manufacturing the protective cap is lower when the compressible inner liner is of a uniform thickness. It is also easier to manufacture a compressible inner liner of a uniform thickness.

The at least one compressible inner liner of the protective cap may be of a varying thickness.

In the context of this disclosure 'varying thickness' means the at least one compressible inner liner has a different thickness is one portion of the inner liner compared to another portion of the inner liner when the protective cap is not being worn. This in contrast to the compressible feature of the inner liner which reduces in volume when being worn if sufficient pressure is applied, for example, if the wearer hit their head. This feature may provide an increased thickness in areas where the head is at a higher risk of injury. For example, if the wearer is working in close proximity to an overhead beam an increased thickness of the inner liner at the area at the top of the head would provide improved comfort to the wearer if they hit their head on the overhead beam. An increased thickness may cause a slight heat build-up on the head, so it may be advantageous to have a thinner inner liner in areas on the side of the head, where the risk of injury may be less. Another advantage of this feature is that the weight of the protective cap is lower, therefore a wearer may be able to move their head with increased flexibility. This provides an improvement in comfort to the wearer.

According to another embodiment, the at least one compressible inner liner of the protective cap consists of two or more discrete elements.

This feature provides that the compressible inner liner is positioned in areas most at risk from injury. When the inner liner is removably attached to the inner surface of the flexible outer layer, each discrete element can be removed, cleaned and replaced separately. This provides ease of use.

According to another embodiment, the two or more discrete elements of the compressible inner liner are reversibly attached to each other.

This feature ensures the inner liner is more secure on the inside surface of the flexible outer layer providing improved comfort to the wearer.

According to another embodiment, the at least one compressible inner liner of the protective cap comprises a polymeric foam material.

This feature ensures the inner liner is compressible and can absorb some of the force if a wearer hits their head. Other advantages of the polymeric foam material is ease of manufacture and the cost of manufacture is lower than other materials.

According to another embodiment, the flexible outer layer of the protective cap comprises a woven material, a non-woven material, or a knitted material.

This feature provides flexibility to the protective cap. The flexible outer layer of the protective cap provides a close fit to the wearer's head therefore improving and maximising the comfort to the wearer. The flexibility provides improved conformability to the wearer's head and again improves comfort compared to known bump caps which are often rigid or semi-rigid and therefore are not conformable. This feature prevents the protective cap from slipping from the wearer's head, further increasing comfort to the wearer. It also provides protection to dirt and other fragments falling from the workpiece.

DETAILED DESCRIPTION DISCLOSURE

Unless explicitly stated otherwise, all embodiments and optional features of the present disclosure can be combined freely.

The disclosure will now be described, by way of example only, and with reference to the following drawings, in which:

FIG. 1 shows a welding helmet 1 which has a face protection member 3 illustrated in a lowered position and a moveable visor 5 illustrated in a non-welding position. The face protection member 3 is sized and shaped to cover a wearer's face and the upper part and lateral sides of the wearer's head. The moveable visor 5 is arranged on an outside of the face protection member 3. The moveable visor is configured to filter those portions of light of a welding arc that would be harmful for a wearer of the welding helmet 1 observing the welding arc through the moveable visor 5. Furthermore, the moveable visor 5 is pivotably suspended at the welding helmet 1 relative to a see-through window 11. The moveable visor 5 is suspended at a pivot mechanism 13 which has a knob 15 for adjusting a friction between the moveable visor 5 and the face protection member 3.

Figure 1:
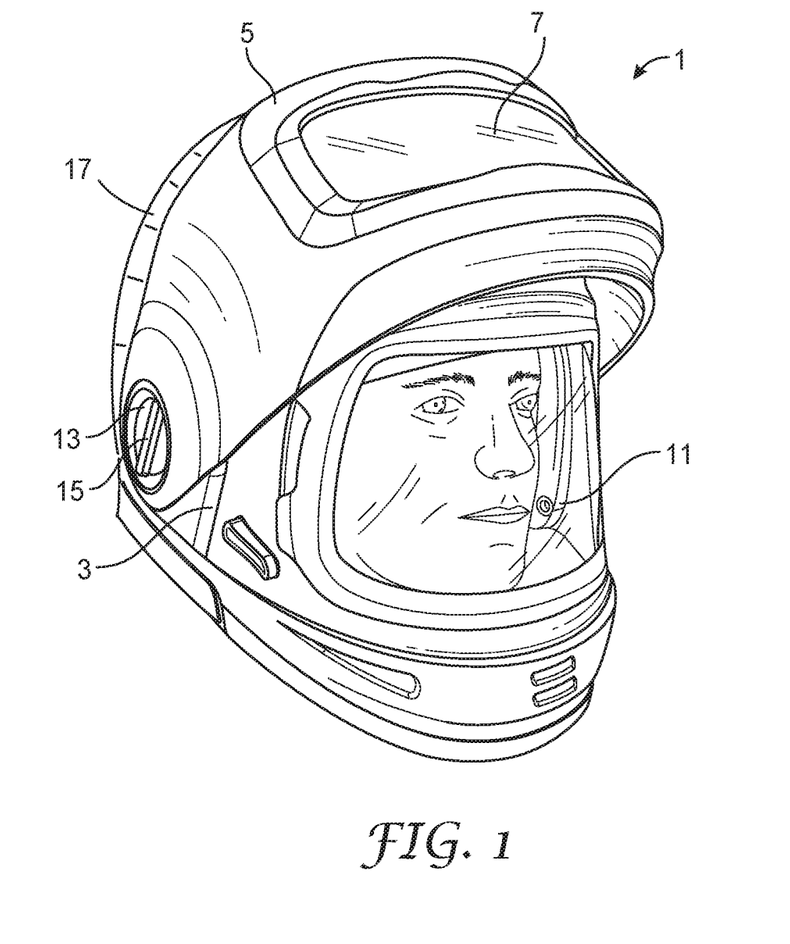
FIG. 1 is a perspective view of a welding helmet.
Figure 2:
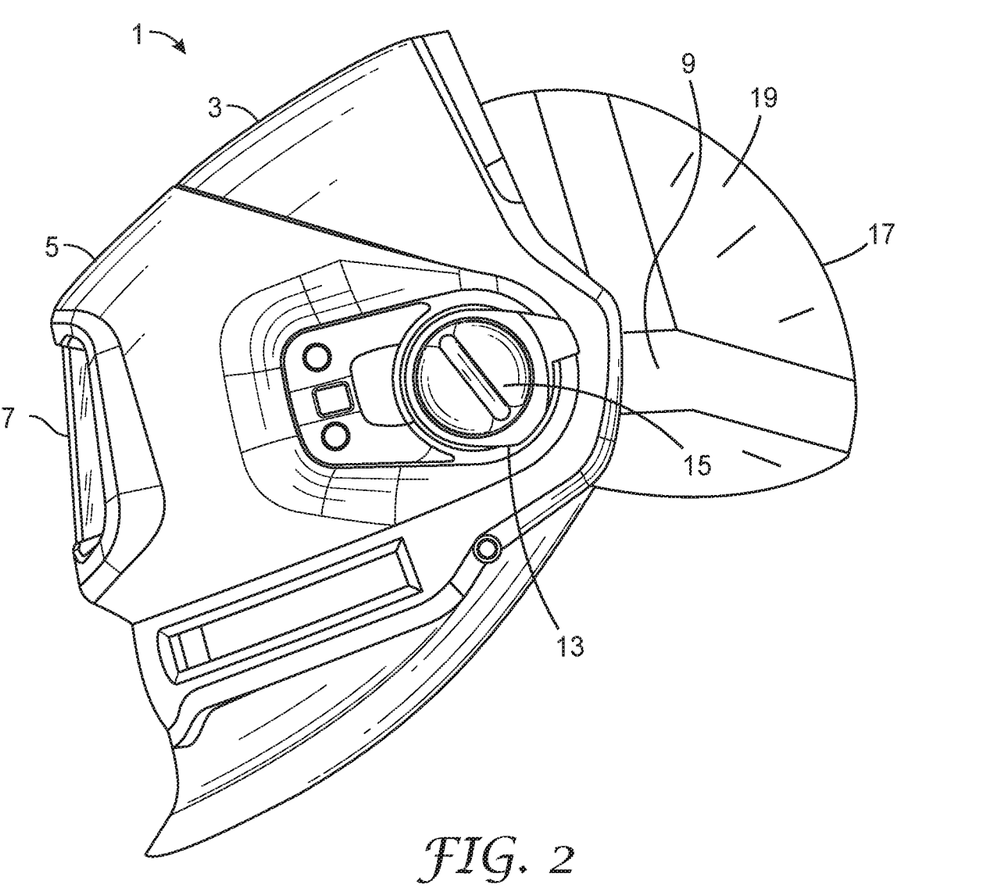
FIG. 2 is a side view of the welding helmet of FIG. 1.

The moveable visor 5 is illustrated in a non-welding position in which the moveable visor 5 does not cover the see-through window 11 provided in the face protection member 3. The moveable visor 3 is moveable between a welding position (as shown in FIG. 2) and the non-welding position of FIG. 1.

The moveable visor 5 comprises an automatic darkening filter 7. The automatic darkening filter 7 allows a wearer to safely observe the welding arc during welding. In the example, the automatic darkening filter 5 is based on two liquid crystal cells. The liquid crystal cells are electrically switchable between a light-state and a dark-state. When switched in the dark-state, the automatic darkening filter 7 blocks a significant amount of light from being transmitted therethrough. This enables a wearer to observe a welding arc by seeing through the automatic darkening filter 7 without risking exposure to harmful light radiation from the welding arc. In the light-state the automatic darkening filter 7 permits a significant amount of light to be transmitted therethrough. Therefore, the automatic darkening filter 7 in the light-state allows the wearer to see under ambient light conditions (in the absence of the welding arc). The two (or more) liquid crystal cells are arranged optically in sequence. This provides for multiplying the darkening effect, in particular in the dark-state, and therefore provides sufficient eye protection from the light radiation.

Further, the welding helmet 1 comprises at least one light sensor (not shown) and an electronic circuitry that causes the liquid crystal cells to switch depending on light recognised by the light sensor(s). In particular, the light sensor may provide a signal to the electronic circuitry depending on the light sensed by the light sensor. The signal provided by the light sensor can typically be correlated to the intensity of light sensed by the light sensor. The electronic circuitry is set up to control the switching of the automatic darkening filter to the dark-state in case the light intensity (and optionally an additional frequency or pulsation) detected by the light sensor is within a predetermined range of values or exceeds a predetermined value. Further, the electronic circuitry is set up to control the switching of the automatic darkening filter to the light-state in case the light intensity detected by the light sensor is outside the predetermined range of values or falls below a predetermined value.

The welding helmet 1 comprises a protective cap 17.

FIG. 2 shows the welding helmet 1 of FIG. 1 with the moveable visor 5 in the welding position. The face protection member 3 of the welding helmet 1 can be lifted or swivelled to an upraised position. The swivelling of the face protection member 3 is provided relative to a head suspension system 9. The headband suspension system is described in more detail with reference to FIG. 4. The protective cap 17 is fitted around the wearer's head, protecting the back of the head without extending to the neck. When the face protection member 3 is lifted to an upraised position, the face protection member 3 partially covers the protective cap 17 (not shown in FIG. 2). When the face protection member 3 is in the welding position, the protective cap is uncovered by the face protection member (shown in FIG. 2).

Figure 3:
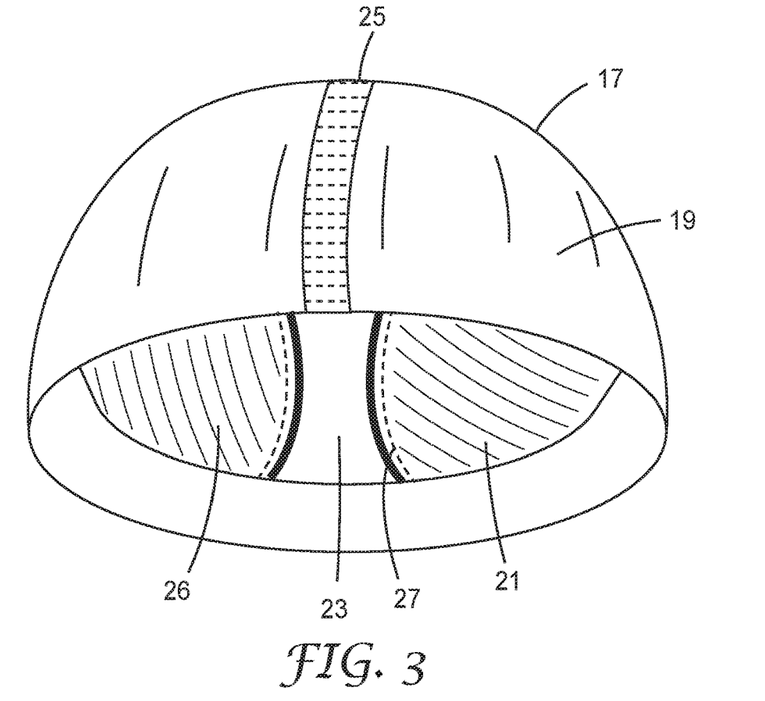
FIG. 3 is a perspective view of the protective cap according to this disclosure.

FIG. 3 shows a perspective view of the protective cap 17 without the welding helmet from underneath the protective cap 17. A flexible outer layer 19 of the protective cap 17 is made from a textile material which can conform to the wearer's head. It is thick enough to protect the wearer's head from dust and small amounts of debris without it being stiff or rigid in any part causing discomfort. The flexible outer layer 19 can be wiped, cleaned or washed. The flexible outer layer 19 has a hook side of a hook and loop attachment means 25 facing to the outside of the protective cap 17 for fixing the protective cap 17 to a headband suspension system 9. The flexible outer layer 19 has an inside surface 23 which faces the wearer's head. A compressible inner liner 21 is attached to the inside surface 23 of the flexible outer layer 19 using sewing means 27. The compressible inner liner 21 is made of a compressible foam material 26 which can absorb small shocks or bumps to the wearer's head by decreasing in volume when a pressure is applied to it. The discrete elements 22, 24 of the compressible inner liner 21 (shown in FIGS. 5 and 7) are of different thicknesses in respect to each other. Discrete element 22 may be thicker than discrete element 24 as it protects the top and back of the wearer's head which may be more susceptible to injury from a hit on the head. A thicker discrete element will have increased compressibility, as it will have a higher change in volume when a pressure is applied.

Figure 4:
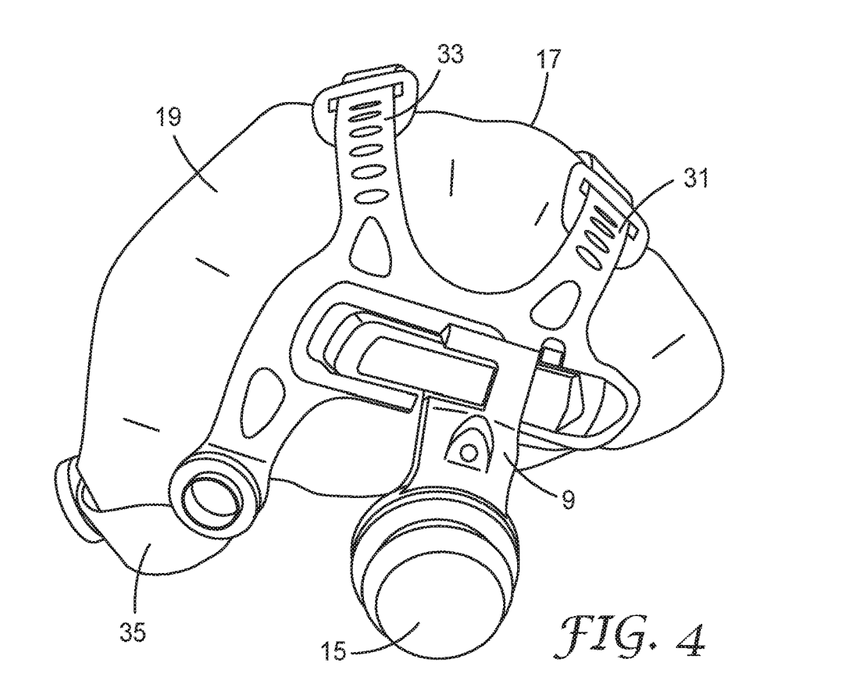
FIG. 4 is a side view of a protective cap and a head suspension system according to this disclosure.

FIG. 4 shows the protective cap 17 attached to a head suspension system 9. In this embodiment, the flexible outer layer 19 of the protective cap 17 is attached to the headband suspension system 9 using the hook and loop attachment means 25 (not shown in FIG. 4). The head suspension system 9 comprises three headbands. There is an adjustable headband 31 located towards the front of the head which can tighten the headband suspension system to fit closer to the front of the head. There is an adjustable headband 33 located at the top of the head which can tighten the headband suspension system to fit closer to the top of the head. There is also an adjustable headband 35 which can tighten the headband suspension system 9 to fit closer to the back of the head. The protective cap is attached to each of the adjustable headbands 31, 33 and 35 of the head suspension system 9. The protective cap 17 is positioned next to the wearer's head and each adjustable headband 31, 33 and 35 can be adjusted around the protective cap 17. The tighter each headband is adjusted the closer the protective cap 17 fits to the wearer's head. The protective cap 17 covers the top of the head and it partially covers the forehead of the face, extending further than headband 31. The protective cap 17 also covers the back of the head without extending to the nape of the neck. It stops in line with headband 35. The flexible outer layer 19 ensures the head suspension system 9 can still provide a comfortable fit to the wearer.

Figure 5:
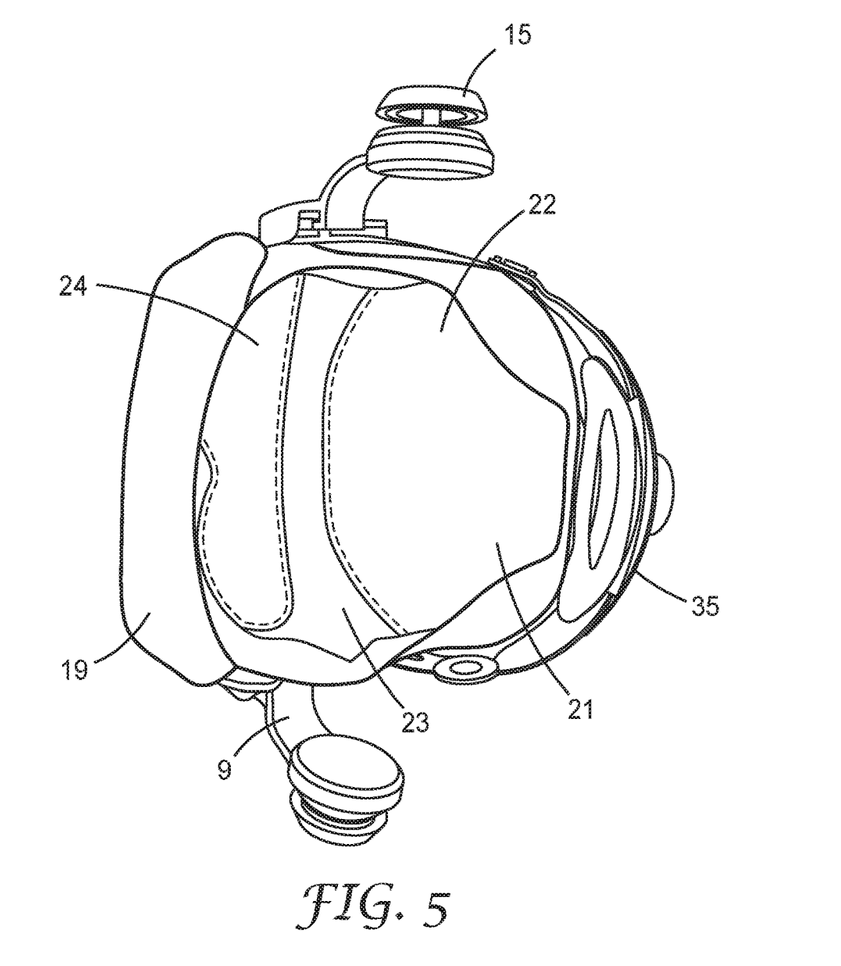
FIG. 5 is another view of the protective cap of FIG. 4.
Figure 7:
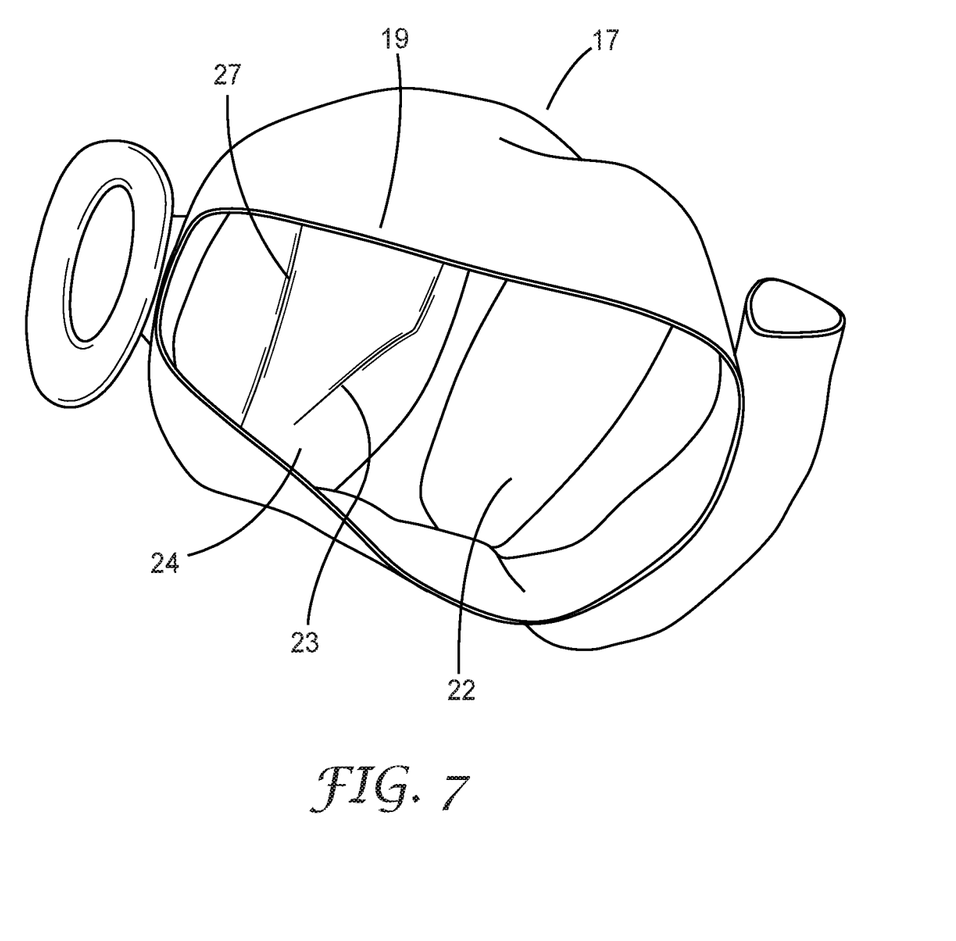
FIG. 7 is another perspective view of the protective cap.

FIG. 5 and FIG. 7 show the inside and outside of the protective cap 17 when it is detached from the head suspension system 9. The compressible inner liner 21 consists of two discrete elements. There is one discrete element 22 located towards the front of the protective cap 17 covering the top of the head and the front of the head. There is another discrete element 24 located towards the back of the protective cap 17 covering the back of the head. The discrete elements 22 and 24 are of the same thickness. The discrete elements 22 and 24 of the compressible inner liner 21 are attached to the inside surface 23 of the flexible outer layer 19 using sewing means 27.

Figure 6:
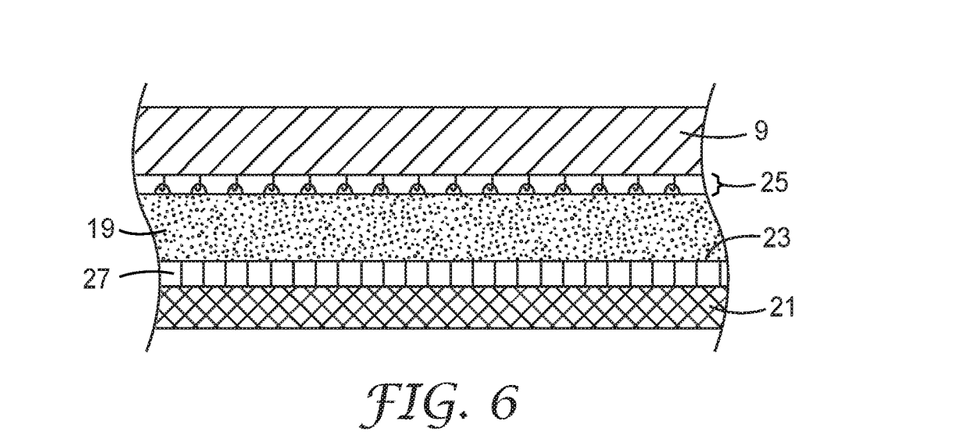
FIG. 6 is a cross section of the protective cap with the flexible outer layer and compressible inner liner attached to the inside surface of the flexible outer layer.

FIG. 6 is a cross section of the protective cap with the flexible outer layer and compressible inner liner attached to the inside surface of the flexible outer layer. In this embodiment, the flexible outer layer 19 of the protective cap 17 is attached to the headband suspension system 9 using a hook and loop attachment means 25. The loop side of the hook and loop attachment means 25 is fixed onto each of the headbands 31, 33 and 35 of the headband suspension system 9, and the hook side of the hook and loop attachment means 25 is fixed to the flexible outer layer 19 of the protective cap 17. In this embodiment the compressible inner liner 21 is attached to the inside surface 23 of the compressible inner liner using sewing means 27.

The invention claimed is:

1. A welding helmet comprising:
   a face protection member moveable between a lowered position, in which the face protection member covers a wearer's face, and an upraised position, in which the face protection member uncovers the wearer's face;
   a headband suspension system for fixing the face protection member to a wearer's head; and
   a protective cap comprising a flexible outer layer and at least one compressible inner liner; wherein the at least one compressible inner liner of the protective cap is of a varying thickness.

2. The welding helmet of claim 1, wherein the face protection member comprises a moveable visor and the moveable visor comprises an automatic darkening filter.

3. The welding helmet of claim 1, wherein the protective cap comprises a first attachment means for attaching the protective cap to the headband suspension system.

4. The welding helmet of claim 1, wherein the first attachment comprises a hook and loop attachment, a sewing attachment, a clip or an adhesive.

5. The welding helmet of claim 1, wherein the protective cap is attached under the headband suspension system.

6. The welding helmet of claim 1, wherein the compressible inner liner of the protective cap is permanently or removably attached to an inside surface of the flexible outer layer of the protective cap.

7. The welding helmet of claim 1, wherein the compressible inner liner of the protective cap is attached to the inside surface of the flexible outer layer of the protective cap using a second attachment.

8. The welding helmet of claim 1, wherein the second attachment is any one of a hook and loop attachment, a sewing attachment, a clip or an adhesive.

9. The welding helmet of claim 1, wherein the at least one compressible inner liner of the protective cap consists of two or more discrete elements.

10. The welding helmet of claim 1, wherein the two or more discrete elements of the compressible inner liner are reversibly attached to each other.

11. The welding helmet of claim 1, wherein the at least one compressible inner liner of the protective cap comprises a polymeric foam material.

12. The welding helmet of claim 1, wherein the flexible outer layer of the protective cap comprises a woven material, a non-woven material or a knitted material.

13. A welding helmet comprising:
   a face protection member moveable between a lowered position, in which the face protection member covers a wearer's face, and an upraised position, in which the face protection member uncovers the wearer's face;
   a headband suspension system for fixing the face protection member to a wearer's head; and
   a protective cap comprising a flexible outer layer and at least one compressible inner liner, wherein the at least one compressible inner liner of the protective cap is of a varying thickness, wherein the at least one compressible inner liner of the protective cap consists of two or more discrete elements.

14. The welding helmet of claim 13, wherein the face protection member comprises a moveable visor and the moveable visor comprises an automatic darkening filter.

15. The welding helmet of claim 13, wherein the protective cap comprises a first attachment for attaching the protective cap to the headband suspension system.

16. The welding helmet of claim 13, wherein the protective cap is attached under the headband suspension system.

17. A welding helmet comprising:
   a face protection member moveable between a lowered position, in which the face protection member covers a wearer's face, and an upraised position, in which the face protection member uncovers the wearer's face;
   a headband suspension system for fixing the face protection member to a wearer's head; and
   a protective cap comprising a flexible outer layer and at least one compressible inner liner, wherein the two or more discrete elements of the compressible inner liner are reversibly attached to each other.

18. The welding helmet of claim 17, wherein the face protection member comprises a moveable visor and the moveable visor comprises an automatic darkening filter.

19. The welding helmet of claim 17, wherein the protective cap comprises a first attachment for attaching the protective cap to the headband suspension system.

20. The welding helmet of claim 17, wherein the protective cap is attached under the headband suspension system.

* * * * *